United States Patent
Puttler et al.

(10) Patent No.: US 6,733,285 B2
(45) Date of Patent: May 11, 2004

(54) ORTHODONTIC APPLIANCE WITH LINGUAL RETAINING GROOVE

(75) Inventors: Oliver L. Puttler, La Crescenta, CA (US); John A. Verdouw, Ontario, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/017,531

(22) Filed: Dec. 14, 2001

(65) Prior Publication Data

US 2003/0113683 A1 Jun. 19, 2003

(51) Int. Cl.$^7$ .................................................. A61C 3/00
(52) U.S. Cl. ................................ 433/8; 433/10; 433/17
(58) Field of Search ............................ 433/8, 9, 10, 11, 433/12, 13, 14, 16, 17, 20, 22

(56) References Cited

U.S. PATENT DOCUMENTS

| | | | |
|---|---|---|---|
| 2,368,851 A | * 2/1945 | Laskin | 433/11 |
| 3,578,744 A | 5/1971 | Wildman | |
| 3,758,947 A | 9/1973 | Kesling | |
| 3,765,091 A | * 10/1973 | Northcutt | 433/9 |
| 3,922,787 A | * 12/1975 | Fischer et al. | 433/15 |
| RE28,889 E | * 7/1976 | Wildman | 433/14 |
| 3,969,821 A | * 7/1976 | Lee et al. | 433/9 |
| 4,107,844 A | 8/1978 | Kurz | |
| 4,820,151 A | 4/1989 | Pospisil | |
| 4,878,840 A | * 11/1989 | Reynolds | 433/9 |
| D306,207 S | 2/1990 | Hannan et al. | |
| 4,927,360 A | 5/1990 | Pospisil | |
| 4,927,362 A | * 5/1990 | Snead | 433/17 |
| 4,963,092 A | 10/1990 | Snead | |
| 5,059,119 A | 10/1991 | Snead | |
| 5,151,028 A | 9/1992 | Snead | |
| 5,230,620 A | * 7/1993 | Watanabe | 433/17 |
| 5,269,681 A | * 12/1993 | Degnan | 433/11 |
| 5,275,557 A | 1/1994 | Damon | |
| 5,913,680 A | 6/1999 | Voudouris | |

FOREIGN PATENT DOCUMENTS

WO  WO 97/42906  11/1997

OTHER PUBLICATIONS

3M Unitek Product Catalog 2001–2002, pp. 3–1 to 3–17.
GAC Orthodontic Catalog Copyright 1997, pp. 58–77.
GAC Orthodontic Products, (1983), pp. A1, E1–E10.
U.S. Ser. No. 09/848,030 filed May 3, 2001.
U.S. Ser. No. 10/017,326, filed Dec. 14, 2001.

* cited by examiner

Primary Examiner—Cary E. O'Connor
(74) Attorney, Agent, or Firm—James D. Christoff (57) ABSTRACT

An appliance used in orthodontic treatment includes a retaining groove that is located directly adjacent a base of the appliance. The retaining groove is useful for keeping a wire segment or other item in place and in contact with a body of the appliance so that the item does not detach from the appliance during the course of treatment. The retaining groove is particularly useful for keeping tieback loops and other items having a thread-like configuration in a captive, compact and snug relationship with the appliance.

39 Claims, 4 Drawing Sheets

ORTHODONTIC APPLIANCE WITH LINGUAL RETAINING GROOVE

BACKGROUND OF THE INVENTION

1. Field of the Invention

This invention relates to an appliance that is fixed to a patient's tooth during the course of orthodontic treatment. The appliance has a retaining groove to hold a wire segment or another item connected to the appliance in place.

2. Description of the Related Art

Orthodontic treatment involves movement of malpositioned teeth to desired locations along the dental arches. Orthodontic treatment provides improved occlusion so that the teeth function better together during chewing. Orthodontic treatment can also greatly enhance the aesthetic appearance of the patient's oral cavity by realigning crooked teeth and eliminating gaps or spaces between adjacent teeth.

One common form of orthodontic treatment is carried out by the use of tiny, slotted appliances known as brackets that are secured to the patient's anterior, cuspid and bicuspid teeth. An archwire is received in the slot of the appliances and forms a track to guide movement of the teeth to desired positions. Ends of the archwires are often received in passageways of small appliances known as buccal tubes that are secured to the patient's molar teeth.

Many orthodontic appliances have small, curved protrusions known as tiewings that extend outwardly from a central body of the appliance. For example, certain brackets have two spaced apart tiewings that extend in a gingival direction (i.e., a direction toward the patient's gingiva or gums). Those brackets also often have two spaced apart tiewings that extend in an occlusal direction (i.e., in a direction toward the outer tips of the patient's teeth). The gingival tiewings are connected to a central body of the bracket along a gingival side of the archwire slot and the occlusal tiewings are connected to the bracket body along an occlusal side of the archwire slot.

Tiewings are commonly used by the orthodontist during treatment to hold the archwire in the archwire slot. To this end, a ligature is placed along the back or lingual side of the occlusal tiewings and the gingival tiewings and is also placed over the front or labial side of the archwire. (As used herein, the word "lingual" refers to a direction toward the patient's tongue, while the word "labial" refers to a direction toward the patient's lips or cheeks.) In many instances, the ligature holds the archwire in contact with the bottom or lingual side of the archwire slot. However, in instances where the tooth is significantly maloccluded and initially located some distance from the archwire, the ligature serves to urge the archwire in a direction toward the bottom of the archwire slot.

In general, there are two types of ligatures in widespread use. One type of ligature is in the form of a tiny elastomeric O-ring. The O-ring is sufficiently flexible such that it can be stretched around and behind the tiewings as well as over the front side of the archwire. Once the O-ring is in place, the inherent memory of the elastomeric material tends to return the O-ring toward its normally compact, unstretched configuration. This contracting force urges the archwire toward the bottom of the archwire slot and also helps to retain the ligature in place.

Other types of ligatures are known as wire ties. These ligatures are made from short lengths of wire such as stainless steel wire having a small cross-sectional diameter. In use, the orthodontic practitioner extends the wire ligature around the backs of the tiewings as well as across the front side of the archwire, and then twists the free ends of the ligature together. Once the ends are twisted together and any slack in the ligature has been removed, the archwire is retained in the archwire slot or is urged toward the same.

The tiewings of the orthodontic appliances described above typically have a concavity in the form of a curved groove or notch that extends along the lingual side of the tiewing. For example, many tiewings have a semi-cylindrical lingual concavity that is oriented such that the central axis of the semi-cylindrical shape is approximately parallel to the longitudinal axis of the archwire slot. In some instances, the opposite side (or labial side) of the tiewing is generally flat and co-planar with a labial side of the appliance body. In other instances, the labial side of the tiewing has a curved configuration complemental to the curved concavity of the lingual side, such that the tiewing has an overall, somewhat hook-shaped or "C"-shaped configuration.

The lingual concavity of the tiewings as described above is generally considered important since it helps to retain the ligature in place during the course of treatment. Ligatures that become detached from appliances in use represent a significant nuisance since they may be inadvertently swallowed by the patient. In addition, appliances that are no longer connected to archwires due to missing ligatures are ineffective in moving the associated tooth, and as a result the length of treatment time may be extended.

As a consequence, manufacturers of orthodontic appliances have often designed and constructed tiewings to reduce the likelihood that the ligature will become detached from the appliance during the course of treatment. To this end, the lingual concavity of the tiewings typically is sufficiently large to extend around a substantial portion (such as one-half) of the periphery of the ligature when considered in cross-sectional reference planes. Ligatures that are deeply seated in the concavity during use are less likely to slip off of the tiewing and become disengaged from the appliance.

However, ligatures are available in a wide variety of cross-sectional sizes and shapes. Wire ligatures typically have a round cross-sectional shape with diameters ranging from about 0.008 in. (0.20 mm) to about 0.014 in. (0.36 mm). Ligatures made from an elastomeric material often have a cross-sectional diameter that is much larger, such as about 0.030 in. (0.76 mm) when relaxed and about 0.020 in. (0.5 mm) when in use. Furthermore, elastomeric ligatures are also known having cross-sectional shapes other than circular (see, e.g., U.S. Pat. No. 3,758,947).

As a result, the tiewings of orthodontic appliances are often provided with relatively large lingual concavities in order to accommodate any one of the wide variety of ligature sizes that might be selected by the orthodontic practitioner. This large lingual concavity tends to increase the overall size of the tiewing. Furthermore, tiewings are also designed with relatively thick cross-sections so that they are less likely to fracture and break off from the body of the appliance during use. Strong tiewings are deemed important because the tiewings are sometimes subjected to large forces, such as when a tiewing encounters a relatively hard food object in the oral cavity while the patient is eating.

Consequently, the tiewings of orthodontic appliances are often bulky in relation to remaining structural aspects of the appliance. The relatively large size of the tiewings is considered a disadvantage, however, because it increases the likelihood of contact with opposing dentition or with appliances mounted on opposing dentition. Tiewings may also contact adjacent soft tissue in the oral cavity and cause an irritation.

Manufacturers of orthodontic appliances have sometimes omitted tiewings when designing buccal tubes. The archwire passageways of buccal tubes are often closed along four sides, in contrast to the archwire passageways or slots of orthodontic brackets that are open along one side. When the ends of the archwires are inserted in the closed passageways, ligatures for connecting the archwire to the buccal tube appliance are not needed. The elimination of tiewings from such appliances helps to ensure that the appliance does not unduly bear against other structure in the oral cavity.

However, there are some instances where orthodontic practitioners prefer to use a buccal tube appliance having tiewings. For example, some buccal tubes for first molar teeth have a passageway that can be opened along one side for converting the buccal tube to a bracket. Opening of the passageway is often carried out in adolescent patients after that patient's adjacent second molar tooth has erupted sufficiently to receive a buccal tube on its surface. Once the passageway of the buccal tube on the first molar tooth has been opened, the tiewings serve to hold a ligature in place.

Additionally, there may be a gap between adjacent teeth at one or more locations along the dental arch. In those instances, the practitioner may elect to install a wire segment known as a "tieback loop" to move teeth along the length of the arch and close the gap. Typically, one side of the tieback loop is connected to a buccal tube, while the opposite side of the loop is connected to an appliance that is located on the opposite side of the gap.

Some practitioners prefer to connect tieback loops to a hook of the buccal tube appliance. However, other practitioners prefer to connect tieback loops to the body of the buccal tube appliance. In those instances, the loop extends along the occlusal, distal and gingival sides of the buccal tube body in a location next to the base. Once the ends of the tieback loop are twisted together to remove slack, the tiewings help ensure that the loop does not slip off the body. Unfortunately, the tiewings are often considered troublesome for the reasons mentioned above.

In the past, a rear portion of some buccal tube appliances extends in a distal direction (i.e., in a direction away from the center of the patient's dental arch) in spaced, overhanging relation to the base. This overhanging portion presents a notch adjacent the base of the appliance which can be used to receive a tieback loop. However, the notch alone is sometimes considered unsatisfactory for ensuring that the tieback loop does not move during the course of treatment.

At present, there is a need in the art for an orthodontic appliance having improved features for securely retaining tieback loops and other items in place as needed. Preferably, such an appliance has an overall relatively compact configuration to reduce the likelihood that it might contact the opposing teeth of the other dental arch, bear against orthodontic appliances that are mounted on the opposing teeth or irritate adjacent soft tissue.

SUMMARY OF THE INVENTION

The present invention is directed to an orthodontic appliance with a retaining groove adjacent a base of the appliance. The groove functions to keep a wire segment or other item in place during the course of treatment. The groove preferably extends along at least two sides of the appliance, and more preferably extends along at least three sides of the appliance next to the base.

The retaining groove of the present invention is particularly useful for keeping an elongated wire segment or other item in a proper orientation on the appliance and in a securely coupled, stationary relationship to the appliance. The groove enables the captive wire or other item to be snugly held against the appliance in a recessed, compact orientation. Examples of suitable wire and other items include tieback loops and structures for the securing a number of teeth and/or orthodontic appliances to each other. The wire or other item may be made of a metallic or polymeric material (including elastomeric materials) so long as its cross-sectional configuration is sufficiently small. The appliance of the invention can be, for example, a buccal tube appliance, a bracket appliance or a self-ligating appliance, including an appliance that lacks tiewings as well as an appliance that has tiewings.

In more detail, the present invention is directed toward an orthodontic appliance that comprises a base and a body extending outwardly from the base. The body has an occlusal side and a gingival side. An elongated archwire passageway for receiving an archwire extends across the body between the occlusal side and the gingival side. The appliance also includes a groove that extends along at least one of the occlusal side and the gingival side in a location adjacent the base. The groove is located in a lingual direction relative to at least one of the occlusal side and the gingival side. The body extends over the groove in a direction that is approximately perpendicular to a labial-lingual reference axis extending through the center of the appliance.

Another aspect of the present invention is also directed toward an orthodontic appliance that comprises a base and a body extending outwardly from the base. The body has an occlusal side and a gingival side. An elongated archwire passageway extends across the body between the occlusal side and the gingival side for receiving an archwire. The appliance further includes a groove for retaining a wire segment or other item in place. The groove is located adjacent the base and has a labial side. The groove extends along at least one of the occlusal side and the gingival side, and the at least one of the occlusal side and the gingival side presents a shoulder that extends over the labial side of the groove.

The present invention is also directed toward an orthodontic appliance that comprises a base and a body extending outwardly from the base. The body has an occlusal side and a gingival side. The appliance also includes an elongated archwire passageway extending across the body between the occlusal side and the gingival side for receiving an archwire. The body includes a neck portion that is located directly adjacent the base and is located in a lingual direction relative to the occlusal side and the gingival side. The neck portion has a certain overall width in an occlusal-gingival direction. The body has an overall width from the occlusal side to the gingival side that is greater than the overall width of the neck portion.

An additional aspect of the present invention is directed toward an orthodontic appliance that includes a base and a body extending outwardly from the base. The body has an occlusal side and a gingival side. An elongated archwire passageway having a generally flat lingual side extends across the body for receiving an archwire. The appliance further includes a groove that extends along the occlusal side and the gingival side of the body. The groove is located directly adjacent the base and has a labial side. The labial side of the groove extends in a direction that is approximately parallel to the lingual side of the archwire passageway.

These and other aspects of the invention are described in more detail below and are illustrated in the accompanying drawings.

DETAILED DESCRIPTION OF THE PREFERRED EMBODIMENTS

An orthodontic appliance according to one embodiment of the invention is illustrated in FIGS. 1–5 and is broadly designated by the numeral 10. The appliance 10 includes a base 12 for attachment to a patient's tooth.

The base 12 has an exterior, lingually-facing surface that is adapted for direct bonding to the patient's tooth. The surface is preferably provided with one or more types of mechanical and/or chemical retention-enhancing means to help ensure that the appliance 10 remains securely bonded to the tooth during the course of treatment. Suitable mechanical and chemical retention means are well known in the art and include, for example, grooves, particles, recesses, undercuts, spheres and adhesion-promoting agents. Preferably, the base 12 has a compound concave contour that is adapted to match the compound convex contour of the patient's tooth surface.

Alternatively, the base 12 may be secured to a band (not shown) or other structure that, in turn, is mounted on the tooth surface. For example, the base 12 may be welded or brazed to a stainless steel band that is placed over the tooth in encircling relationship. The use of a band helps ensure that the appliance 10 does not become detached from the associated tooth during the course of treatment.

The appliance 10 also includes a body 14 that extends outwardly from the base 12 in a labial direction. The body 14 includes an occiusal side 16, a labial side 18 and a gingival side 20. The body also includes a mesial side or end 22 and a distal side or end 24. As shown for example in FIG. 2, the occlusal side 16 and the distal side 24 extend in mesial-distal directions parallel to each other.

An elongated archwire passageway 26 extends across the body 14 from the mesial end 22 to the distal end 24. The archwire passageway 26 lies between the occlusal side 16 and the gingival side 20. The archwire passageway 26 is also located in a lingual direction relative to the labial side 18.

The body 14 includes a neck portion 28 that is directly adjacent the base 12. The neck portion 28 is located in a lingual direction relative to the archwire passageway 26. Preferably, the neck portion 28 presents rounded corners when considered in a reference plane that is perpendicular to a labial-lingual reference axis extending through the middle of the appliance 10.

Figures 1, 2, 3, 4:
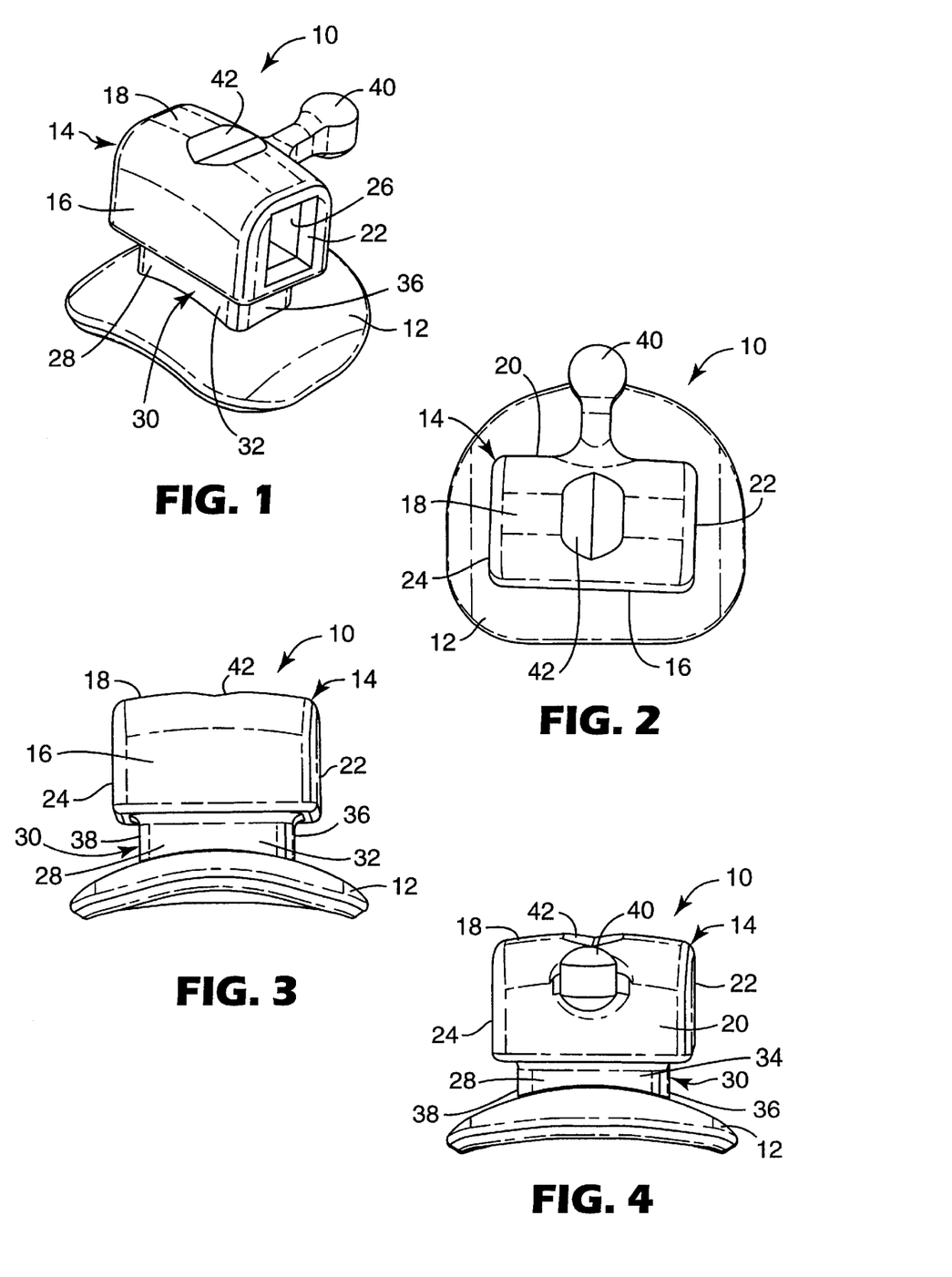
FIG. 1 is a perspective view of an orthodontic appliance according to one embodiment of the invention, looking at the appliance toward its occlusal, mesial and labial sides.
FIG. 2 is an elevational view of the appliance depicted in FIG. 1, looking at the appliance toward its labial side.
FIG. 3 is a elevational view of the appliance shown in FIGS. 1 and 2, looking at the appliance toward its occlusal side.
FIG. 4 is an elevational view of the appliance shown in FIGS. 1–3, looking at the appliance toward its gingival side.

As can be appreciated by reference to FIGS. 1, 3 and 4, the neck portion 28 has an overall length in a mesial-distal direction that is smaller than the largest overall mesial-distal length of the body 14. In the illustrated embodiment, the neck portion 28 has a mesial-distal length that is smaller than the mesial-distal length of the occlusal side 16, the labial side 18, the gingival side 20 and the archwire passageway 26.

Figure 5:
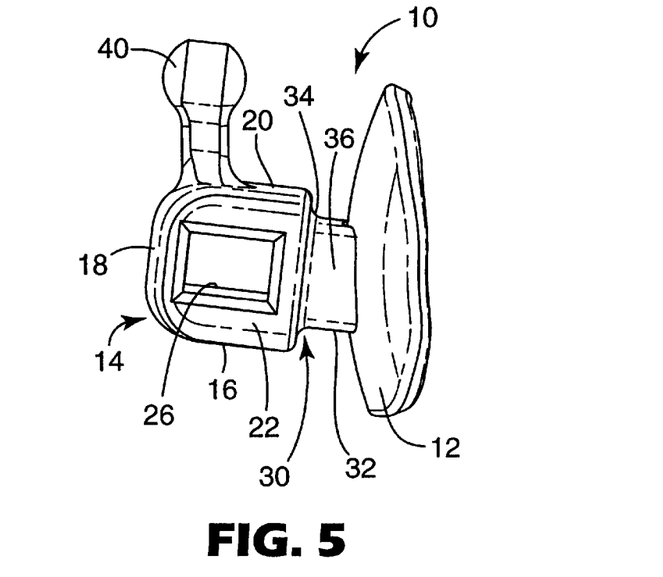
FIG. 5 is an elevational view of the appliance shown in FIGS. 1–4, looking at the appliance toward its mesial side.

The neck portion 28 also has an overall width in an occlusal-gingival direction that is less than the largest overall occlusal-gingival width of the body 14. Specifically, the occlusal-gingival width of the neck portion 28 is less than the distance in an occlusal-gingival direction between the exterior surfaces of the occlusal side 16 and the gingival side 20. This relationship is illustrated in FIGS. 1 and 5.

The appliance 10 also includes a lingual retaining groove 30 for retaining a wire segment or other item in place. The groove 30 is located directly adjacent the base 12 and extends along at least one of the sides 16, 20. In the embodiment shown in the drawings, the groove 30 extends along and below both of the sides 16, 20 as well as along both of the ends 22, 24.

In more detail, the groove 30 includes an occlusal section 32 that is located in a lingual direction relative to the occlusal side 16 and is located in an occlusal direction relative to the neck portion 28. The groove 30 also has a gingival section 34 that is located in a lingual direction relative to the gingival side 20 and in a gingival direction relative to the neck portion 28. The groove 30 further includes a mesial section 36 that is located in a lingual direction relative to the mesial end 22 and in a mesial direction relative to the neck portion 28. Additionally, the groove 30 includes a distal section 38 that is located in a lingual direction relative to the distal end 24 and in a distal direction relative to the neck portion 28. As shown for example in FIG. 5, the occlusal section 32 and the gingival section 34 of the groove 30 are both located lingually of the lingual side of the archwire passageway 26.

The occlusal side 16 presents an elongated shoulder that overhangs the occlusal section 32 of the groove 30. Similarly, the gingival side 20 presents an elongated shoulder that overhangs the gingival section 34 of the groove 30. The mesial end 22 and the distal end 24 present shoulders that overhang the mesial section 36 and the distal section 38 respectively. Each of the shoulders presented by the sides 16, 20 and the ends 22, 24 extends in a respective reference plane that is preferably approximately perpendicular, and more preferably perpendicular, to a reference axis extending in a labial-lingual direction through the center of the appliance 10.

Preferably, the groove 30 has a height in a labial-lingual direction that is sufficient for retaining an elongated wire segment or other item in place. Preferably, the overall labial-lingual height of the groove 30 is at least 0.005 inch (0.13 mm) and more preferably is at least 0.008 inch (0.2 mm). In the illustrated embodiment, the minimum overall height of the groove 30 is located in a center region of the occlusal section 32 and the gingival section 34 due to the convex shape of the adjacent section of the base 12 as shown in FIGS. 1, 3 and 4.

Preferably, the groove 30 has an overall width in a direction away from the neck portion 28 that is at least 0.005 inch (0.13 mm) and more preferably is at least 0.008 inch (0.2 mm). For the occlusal section 32 and the gingival section 34, this width is determined by measuring along an occlusal-gingival reference axis in a direction away from the neck portion 28 and to the outer corner of the overlying shoulder. For the mesial section 36 and the distal section 38, this width is determined by measuring along a mesial-distal reference axis in a direction away from the neck portion 28 and to the outer corner of the overlying shoulder.

The appliance 10 also includes a hook 40 for optional connection to another orthodontic device. Examples of suitable devices include coil springs and elastomeric force modules that are connected to other appliances in the patient's oral cavity. Optionally, such devices have an end section with a hole or opening that receives the hook 40, although other types of connections are also possible.

The hook 40 in this embodiment has an overall straight configuration that extends in a gingival direction away from the gingival side 20 of the body 14. The outer end of the hook 40 has an enlarged head. Preferably, all of the surfaces of the hook 40 are smoothly rounded to avoid irritating soft tissue in the oral cavity.

Optionally, the appliance 10 includes one or more positioning notches to help align the appliance 10 to the patient's tooth or to a band in instances where the appliance 10 is assembled to a band. In the embodiment shown in the drawings, the appliance 10 includes a labial groove or notch 42 that is adapted to received the end of a positioning tool. Once the appliance 10 is placed on the patient's tooth, the practitioner can place the end of the positioning tool in the notch 42 in order to exert a force on the appliance 10 as may be needed to precisely shift it to a desired location on the tooth structure.

Figure 6:
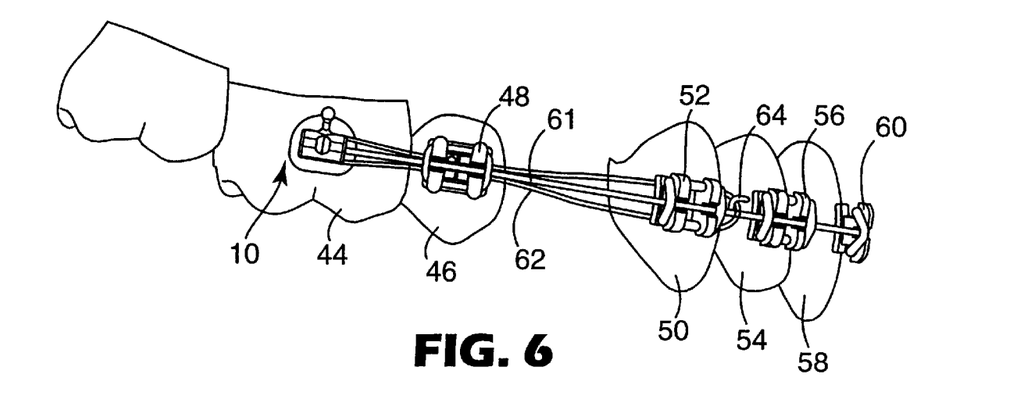
FIG. 6 is a reduced elevational view showing for exemplary purposes the appliance of FIGS. 1–5 as it might appear when mounted on an upper first molar tooth of a patient undergoing orthodontic treatment, and also showing a set of additional appliances mounted on other teeth, an archwire connected to the appliances and a tieback loop used to close a space between two adjacent teeth of the patient.

FIG. 6 illustrates an example of use of the appliance 10 for a patient undergoing orthodontic therapy. In this example, the appliance 10 is directly bonded to a patient's first upper right molar tooth 44.

The remaining teeth in FIG. 6 each receive an orthodontic bracket. In particular, a bicuspid tooth 46 receives a bracket 48, a cuspid tooth 50 receives a bracket 52, a lateral tooth 54 receives a bracket 56 and a central tooth 58 receives a bracket 60. For exemplary purposes, the illustrated brackets 48, 52, 56, 60 are metallic brackets that are directly bonded to the patient's tooth enamel, although other brackets and/or methods of connection could be utilized.

An archwire 61 is connected to the slots of the brackets 48, 52, 56, 60 and is inserted in the passageway 26 of the appliance 10. In this example, the patient has a gap between the bicuspid tooth 46 and the cuspid tooth 50. During orthodontic treatment, it is often desired to close such spaces for aesthetic purposes. Moreover, if the space is not closed, the teeth may drift over a period of time and assume new positions that are crooked or otherwise unsatisfactory.

Consequently, the orthodontic practitioner faced with the scenario presented in FIG. 6 may elect to use a tieback loop to move the teeth together and close the gap. The tieback loop in FIG. 6 comprises a wire segment 62 that interconnects the appliance 10, the bicuspid bracket 48 and the cuspid bracket 52. An example of a suitable wire segment 62 is stainless steel wire having a diameter in the range of about 0.010 in. (0.25 mm) to about 0.014 in. (0.35 mm).

The wire segment 62 is installed along a path that extends along the gingival and occlusal sides of the brackets 48, 52 and the gingival side 20, the distal end 24 and the occlusal side 16 of the appliance 10. More specifically, for the appliance 10, the wire segment is placed in the occlusal section 32, the gingival section 34 and the distal section 38 of the groove 30. The wires segment is also placed behind (i.e., on a lingual side of) the hook 40 as well as behind the end portion of the archwire 61 that protrudes outwardly from the passageway 26 in a distal direction. In FIG. 6, that distal end portion of the archwire 61 is depicted as bent in an angle in a direction toward the patient's gingiva.

In this example, an auxiliary hook 64 has been secured to an archwire 61 in a location between the cuspid bracket 52 and the lateral bracket 56. The auxiliary hook 64 is secured to the archwire 61 by a spot welding operation, although other types of connections (such as cinch-type connections) are also possible. The ends of the wire segment 62 are then twisted together in a location adjacent the hook 64 in order to remove excess slack in the installed wire segment 62 and tightly secure the assembly together.

The present invention is an advantage, in that the forces exerted (or resisted) by the wire segment 62 lie along a path that is essentially collinear with the curved longitudinal axis of the archwire 61. As such, undesirable rotation or other movements of the teeth 44, 46, 50 may be avoided. Moreover, the wire segment 62 when arranged as shown in FIG. 6 forms a relatively compact assembly with the appliance 10 and the associated brackets 48, 52.

By way of comparison, it is possible for the distal end of the wire segment 62 to extend around the hook 40 of the appliance 10 instead of in a path along the occlusal side 16, the distal end 24 and the gingival side 20 of the appliance 10. However, the resultant force exerted or resisted by the wire segment 62 in that instance is not as aligned with the longitudinal axis of the archwire 61 as it is in the arrangement depicted in FIG. 6. As a consequence, one or more of the teeth 44, 46, 50 may tilt or pivot in one or more directions to an undesirable new orientation.

Preferably, the body 14 (including the neck portion 28 and the hook 40) is integrally made as a single, unitary component. The body 14 and the base 12 are either integrally made as a single component or are manufactured separately and then assembled together. Preferred manufacturing processes for making the body 14 include casting techniques, metal injection molding techniques and machining techniques, using a corrosion-resistant alloy such as an alloy made of stainless steel (e.g., no. 316 or 17-4 stainless steel). If the base 12 is manufactured separately and not intended for attachment to a band, the base 12 may be made from a section of fine wire mesh that optionally includes a foil backing.

The embodiment of the invention that is depicted in FIGS. 1–6 lacks tiewings and consequently presents a relatively compact overall configuration. However, tiewings could be added to the body 14 if desired. In addition, the appliance 10 may include other features as well, such as auxiliary tubes or passages for attachment to headgear or other appliances. The archwire passageway 26 of the appliance 10 may optionally extend at a certain angle relative to the base 12 to provide what is known in the art as torque or offset.

Figure 7:
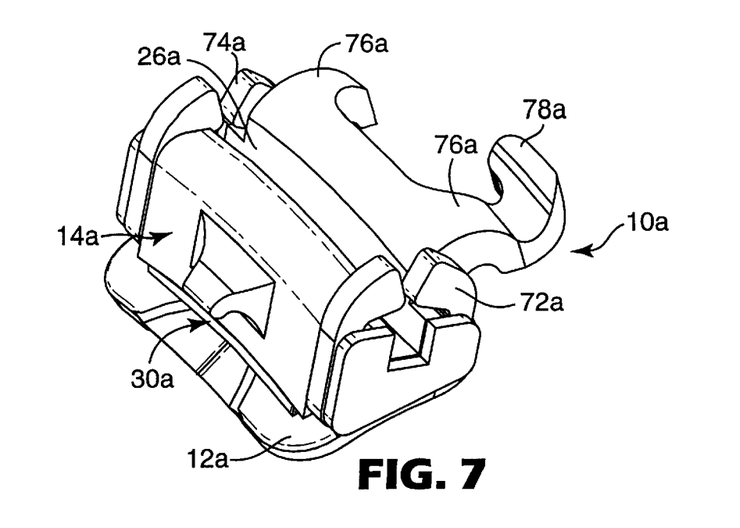
FIG. 7 is a perspective view of an orthodontic appliance according to another embodiment of the invention, looking at the appliance toward its occlusal, labial and mesial sides.
Figure 8:
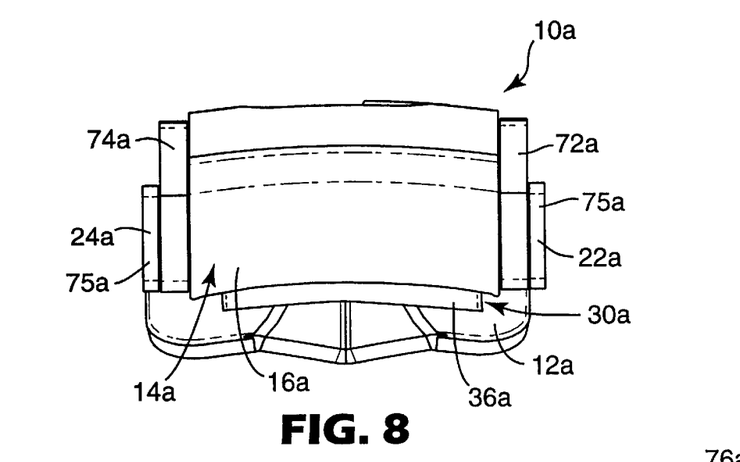
FIG. 8 is an elevational view of the appliance shown in FIG. 7, looking at the appliance toward its occlusal side.
Figure 9:
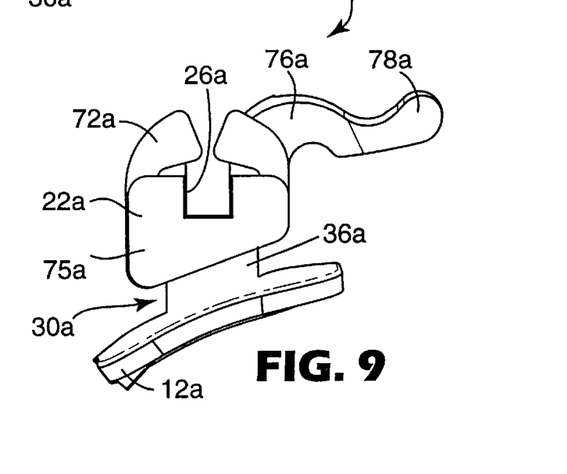
FIG. 9 is an elevational view of the appliance shown in FIGS. 6–7, looking at the appliance toward its mesial end.

An orthodontic appliance 10a according to another embodiment of the invention is illustrated in FIGS. 7–9. The appliance 10a includes a base 12a and a body 14a that extends outwardly from the base 12a. The body includes an occlusal side 16a and a gingival side (not shown). The body 14a also includes a mesial end 22a and a distal end 24a (as further described below). An elongated archwire passageway 26a extends in a generally mesial-distal direction across the body 14a from the mesial end 22a to the distal end 24a.

The appliance 10a is of a type known as a "self-ligating" bracket. To this end, the appliance 10a has a latch that comprises a mesial spring clip 72a and a distal spring clip 74a. When an orthodontic archwire (not shown) is urged in a direction toward the bottom of the archwire passageway 26a, the clips 72a, 74a deflect and spread open to enable the archwire to be moved fully into the passageway 26a. Once the archwire is seated in the passageway 26a, the inherent resiliency of the clips 72a, 74a causes the same to shift to their relaxed, closed position as depicted in FIGS. 7–9 for retaining the archwire in the passageway 26a.

Preferably, the sides of the clips 72a, 74a deflect outwardly to a slot-open orientation and release the archwire from the archwire passageway 26a whenever the force exerted by the archwire on the appliance 10a exceeds a certain minimum value. The minimum value is sufficiently high to prevent the archwire from unintentionally releasing from the archwire passageway 26a during the normal course of orthodontic treatment. As such, the archwire can exert forces on the appliance 10a sufficient to carry out the intended treatment program and move the associated tooth as desired. Preferably, the clips 72a, 74a release the archwire from the archwire passageway 26a in a direction perpendicular and away from the lingual side of the archwire passageway 26a whenever the archwire exerts a force in the same direction on the appliance 10a that is in the range of about 0.2 lb (0.1 kg) to about 11 lbs (5 kg), more preferably in the range of about 0.4 lb (0.2 kg) to about 5.5 lbs (2.5 kg), and most preferably in the range of about 0.4 lb (0.2 kg) to about 2.7 lbs (1.25 kg).

To determine the force to release the archwire from the clips 72a, 74a, an elongated section of archwire is selected having an area in longitudinally transverse section that is complemental to (i.e., substantially fills) the cross-sectional area of the archwire passageway 26a. Next, a sling is constructed and is connected to the archwire section in two spaced apart locations that are closely adjacent but not in contact with the mesial and distal ends of the appliance 10a. Optionally, the sling is welded or brazed to the archwire section. Next, the sling is pulled away from the appliance 10a while the appliance 10a is held in a stationary position, taking care to ensure that the longitudinal axis of the archwire section does not tip relative to the longitudinal axis of the archwire passageway 26a. The force to release the archwire from the clips 72a, 74a is determined by use of an Instron testing apparatus connected to the sling, using a crosshead speed of 0.5 in/mm (1.3 cm/min).

Preferably, the minimum value for self-release (i.e., self-opening) of the clips 72a, 74a is together substantially less than the force required in the same direction to debond the appliance 10a from the associated tooth in instances where the appliance 10a is directly bonded to the tooth surface. The minimum value for self-release of the clips 72a, 74a is preferably less than about one-half of the force required in the same direction to debond the appliance 10a from the associated tooth. For example, if the expected bond strength of the adhesive bond between the appliance 10a and the associated tooth is 16 lbs (7.3 kg) in a buccolabial direction, the clips 72a, 74a are constructed to self-release the archwire whenever the archwire exerts a force in the same buccolabial direction on the appliance 72a, 74a that is somewhat greater than about 8 lbs (3.6 kg).

The self-releasing clips 72a, 74a are a benefit to the practitioner, in that the likelihood of spontaneous debonding of the appliance 10a is substantially reduced. For example, if the practitioner attempts to place a relatively large archwire in the archwire passageway 26a and the clips 72a, 74a open and self-release the archwire as soon as the practitioner releases the archwire, the practitioner can then use an archwire with less stiffness in its place. As another example, if the archwire is initially held in the passageway 26a by the clips 72a, 74a and the archwire subsequently exerts a larger force on the appliance 10a (as may occur, for example, when the archwire encounters a hard object such as when the patient is chewing relatively hard food), the clips 72a, 74a will deflect to their slot-open orientations to release the archwires so that the appliance 10a does not debond from the tooth. Treatment can then be resumed by merely replacing the archwire in the archwire passageway 26a without the need to rebond the base 12a of the appliance 10a to the associated tooth.

Each clip 72a, 74a is preferably made from a flat annealed superelastic material having a pickled surface. Preferably, the superelastic material is nitinol having a nickel content of 55.97% by weight and an $A_f$ of $10°±5°$ C. The nitinol is cold worked to 37.5% and has a thickness in the range of about 0.012 in. (0.3 mm) to about 0.016 in. (0.4 mm). The clips 72a, 74a are first cut in a rough cutting EDM process, and then cut along their edges for an additional one or more times using an EDM process in order to smooth the edges. As another option, the clips 72a, 74a are cut from a section of tubing that is made from a shape memory alloy. Suitable shape memory alloys include alloys of nitinol and beta-titanium. The tubing is cut with a slot to form the opposed arm portions that are best shown in FIGS. 7 and 9.

Other details and features of the latch and the clips 72a, 74a are set out in applicant's co-pending U.S. patent application entitled "ORTHODONTIC APPLIANCE WITH SELF-RELEASING LATCH", U.S. Ser. No. 09/848,030, which is expressly incorporated by reference herein.

The clips 72a, 74a are each held in place by a cap 75a. In this embodiment, the caps 75a are considered as part of the body 14a and provide the mesial end 22a and the distal end 24a as mentioned above. The caps 75a are fixed to protrusions that extend in a mesial-distal direction from the central section of the body 14a, and the protrusions are arranged to retain the clips 72a, 74a in place. For example, protrusions may be provided along the sides of the archwire passageway 26a as well as along a portion or all of the lingual side of the clips 72a, 74a. The protrusions may be integral with either the central section or the caps 75a and then fixed to the other of the central section or the caps 75a by a welding or brazing operation.

The appliance 10a also includes a retaining groove 30a that extends along a path that is located beneath the occlusal side 16a and the gingival side (i.e., lingually of the occlusal side 16a and the gingival side). Preferably, the retaining groove 30a also extends beneath the mesial end 22a and the distal end 24a. The retaining groove 30a is located next to a neck portion 36a of the body 14a. The body 14a also presents shoulders that extend over the groove 30a in directions along a reference plane that is approximately perpendicular to a labial-lingual reference axis extending through the center of the appliance 10a. Alternatively, this reference plane is approximately parallel to the bottom or lingual side of the archwire passageway 26a.

The appliance 10a also includes two tiewings 76a that are connected to the gingival side 20a of the body 14a. The mesial tiewing 76a is integrally connected to a hook 78a. The tiewings 76a are similar to tiewings of conventional brackets known in the art. The tiewings 76a are useful, for example, in initial stages of treatment in instances where the appliance 10a is located a substantial distance from the archwire as might occur when the tooth is severely maloccluded. In those instances, the tiewings 76a together with the retaining groove 30a can be used together with a ligature for establishing a connection between the appliance 10a and the archwire. However, the tiewings 76a are not necessary and may be omitted from the appliance 10a if desired.

Figure 10:
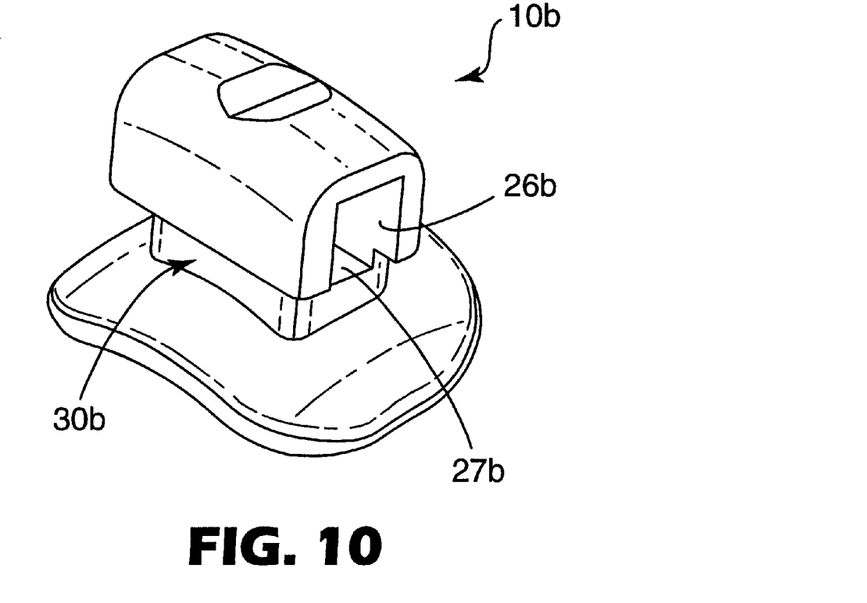
FIG. 10 is a perspective view of an orthodontic appliance according to yet another embodiment of the invention, looking at the appliance toward its occlusal, labial and mesial sides.
Figure 11:
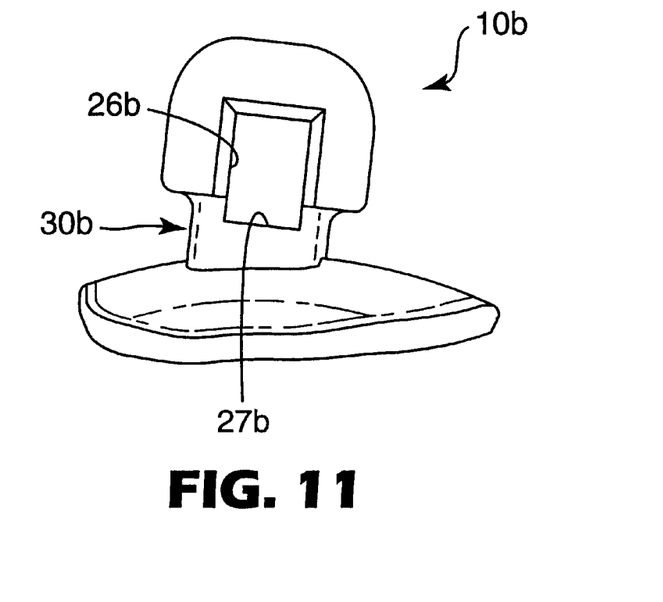
FIG. 11 is an elevational view of the appliance shown in FIG. 10, looking at the appliance toward its mesial end.

An orthodontic appliance 10b according to another embodiment of the invention is illustrated in FIGS. 10 and 11. The appliance 10b is essentially the same as the appliance 10 described above except for the aspects noted below.

The appliance 10b has an archwire passageway 26b with a lingual side 27b. The appliance also has a groove 30b that is similar to the grooves 30, 30a mentioned above. However, the lingual side 27b is located below (i.e. in a lingual direction) relative to the labial side of the groove 30b.

The appliance 10b is especially advantageous in instances where a low profile appliance is desired. An example includes, but is not limited to, use on a first bicuspid tooth. Additionally, the appliance 10b as illustrated does not have a hook so that the likelihood of interference with gingival tissue is reduced. However, the appliance 10b could have a hook if desired.

The grooves 30, 30a, 30b as described above can also be advantageously used to retain items other than tieback loops for closing spaces between adjacent teeth. For example, the grooves 30, 30a, 30b may be used to hold in captive relationship a wire segment that secures a number of teeth together, as may be desired to serve as anchorage for one or more other orthodontic appliances. The grooves 30, 30a, 30b may also serve to retain other certain elongated members in place along the sides of the body that are connected to other teeth, or serve as a point of connection for other devices used during the course of orthodontic treatment.

The examples described above are intended to exemplify the various aspects and benefits of the invention. However, those skilled in the art may recognize that a number of variations and additions to the appliances described above may be made without departing from the spirit of the invention. Accordingly, the invention should not be deemed limited to the specific embodiments set out above in detail, but instead only by a fair scope of the claims that follow along with their equivalents.

What is claimed is:

1. An orthodontic appliance for a molar tooth comprising:
    a base;
    a body extending outwardly from the base, the body having an occlusal side, a gingival side, a mesial end and a distal end;
    an elongated archwire passageway extending across the body between the occlusal side and the gingival side for receiving an archwire, wherein the passageway includes a labial side that is closed; and
    a groove extending in a mesial-distal direction along both the occlusal side and the gingival side of the body, the groove being located adjacent the base and in a lingual direction relative to the occlusal side and the gingival side, wherein the body extends over the groove in a direction that is approximately perpendicular to a labial-lingual reference axis extending through the center of the appliance, and wherein the groove extends along at least one of the mesial end and the distal end, the groove being located in a lingual direction relative to the at least one of the mesial end and the distal end.

2. An orthodontic appliance according to claim 1 wherein the groove extends along both the mesial end and the distal end, the groove being located in a lingual direction relative to both the mesial end and the distal end.

3. An orthodontic appliance according to claim 2 wherein the groove is located in a lingual direction relative to both the mesial end and the distal end.

4. An orthodontic appliance according to claim 1 wherein the groove has a height along a labial-lingual reference axis that is at least about 0.005 inch.

5. An orthodontic appliance according to claim 1 wherein the groove has a width along an occlusal-gingival reference axis that is at least about 0.005 inch.

6. An orthodontic appliance according to claim 1 wherein the groove has a certain length in a mesial-distal direction, and wherein the archwire passageway has a length in a mesial-distal reference axis that is larger than the mesial-distal length of the groove.

7. An orthodontic appliance according to claim 1 wherein the body includes a neck portion that is located directly adjacent the base and wherein at least one of the occlusal side and the gingival side extends past the neck portion in an occlusal-gingival direction.

8. An orthodontic appliance according to claim 1 wherein at least one of the occlusal side and the gingival side presents a shoulder that overhangs the groove.

9. An orthodontic appliance according to claim 1 wherein the occlusal side and the gingival side present a shoulder that overhangs the groove.

10. An orthodontic buccal tube appliance comprising:
    a base;
    a body extending outwardly from the base, the body having an occlusal side and a gingival side that extend in mesial-distal directions parallel to each other, wherein the body includes a neck portion that is located adjacent the base, wherein the neck portion has an overall length in a mesial-distal direction that is less than the largest overall mesial-distal length of the body;
    an elongated archwire passageway extending across the body between the occlusal side and the gingival side for receiving an archwire, the archwire passageway having a lingual side; and
    a groove for retaining a wire segment or other item in place, the groove having an occlusal section extending along the occlusal side and a gingival section extending along the gingival side of the body, the groove being located directly adjacent the base and being located in a lingual direction relative to both the occlusal side and the gingival side, wherein the occlusal side and the gingival side each present a shoulder that extends over the groove in a labial direction, and wherein the occlusal section and the gingival section of the groove are located lingually of the lingual side of the archwire passageway.

11. An orthodontic appliance according to claim 10 wherein the body includes a mesial end and a distal end and wherein the groove extends along at least one of the mesial end and the distal end, the groove being located in a lingual direction relative to the at least one of the mesial end and the distal end.

12. An orthodontic appliance according to claim 11 wherein the groove is located in a lingual direction relative to both the mesial end and the distal end.

13. An orthodontic appliance according to claim 10 wherein the groove has a height along a labial-lingual reference axis that is at least about 0.005 inch.

14. An orthodontic appliance according to claim 10 wherein the groove has a width along an occlusal-gingival reference axis that is at least about 0.005 inch.

15. An orthodontic appliance according to claim 10 wherein the groove has a certain length in a mesial-distal direction, and wherein the archwire passageway has a length in a mesial-distal direction that is greater than the mesial-distal length of the groove.

16. An orthodontic appliance according to claim 10 wherein the occlusal side and the gingival side extends past the neck portion in an occlusal-gingival direction.

17. An orthodontic appliance according to claim 10 and including a latch for releasably retaining an archwire in the archwire passageway.

18. An orthodontic appliance according to claim 10 wherein the appliance is an orthodontic bracket.

19. An orthodontic appliance according to claim 10 wherein the bracket is a self-ligating bracket.

20. An orthodontic appliance comprising:
a base;
a body extending outwardly from the base, the body having an occlusal side and a gingival side that extend in mesial-distal directions parallel to each other, wherein the body includes a neck portion that is located adjacent the base, wherein the neck portion has an overall length in a mesial-distal direction that is less than the largest overall mesial-distal length of the body;
an elongated archwire passageway extending across the body between the occlusal side and the gingival side for receiving an archwire, the archwire passageway having a lingual side;
a groove for retaining a wire segment or other item in place, the groove having an occlusal section extending along the occlusal side and a gingival section extending along the gingival side of the body, the groove being located directly adjacent the base and being located in a lingual direction relative to both the occlusal side and the gingival side, wherein the occlusal side and the gingival side each present a shoulder that extends over the groove in a labial direction, and wherein the occlusal section and the gingival section of the groove are located lingually of the lingual side of the archwire passageway and wherein the passageway includes a labial side that is closed.

21. An orthodontic assembly comprising:
an orthodontic appliance including
a base;
a body extending outwardly from the base, the body having an occlusal side and a gingival side; and
an elongated archwire passageway extending across the body between the occlusal side and the gingival side for receiving an archwire, wherein the body includes a neck portion that is located directly adjacent the base and is located in a lingual direction relative to the occlusal side and the gingival side, wherein the neck portion has a certain overall width in an occlusal-gingival direction, and wherein the body has an overall width from the occlusal side to the gingival side that is greater than the overall width of the neck portion; and
a tieback loop extending along the neck portion.

22. An orthodontic assembly according to claim 21 wherein the occlusal side extends in an occlusal direction past the neck portion and wherein the gingival side extends past the neck portion in a gingival direction.

23. An orthodontic assembly according to claim 21 wherein the body includes a mesial end and a distal end, and wherein the neck portion has a certain overall length in a mesial-distal direction, and wherein the body has an overall length in a mesial-distal direction that is greater than the overall length of the neck portion.

24. An orthodontic assembly according to claim 23 wherein the appliance includes a groove that is located in a lingual direction relative to both the mesial end and the distal end, and wherein the tieback loop is received in the groove.

25. An orthodontic assembly according to claim 21 wherein the appliance includes a groove that is located in a lingual direction relative to both the occlusal side and the lingual side, wherein the groove has a height along a labial-lingual reference axis that is at least about 0.005 inch, and wherein the tieback loop is received in the groove.

26. An orthodontic assembly according to claim 21 wherein the appliance includes a groove that is located in a lingual direction relative to both the occlusal side and the lingual side, wherein the groove has a width along an occlusal-gingival reference axis that is at least about 0.005 inch, and wherein the tieback loop is received in the groove.

27. An orthodontic assembly according to claim 26 wherein the groove has a certain length in a mesial-distal direction, and wherein the archwire passageway has a length in a mesial-distal direction that is larger than the mesial-distal length of the groove.

28. An orthodontic assembly according to claim 21 wherein the passageway includes a labial side that is closed.

29. An orthodontic assembly according to claim 21 wherein the passageway includes a labial side that is at least partially open.

30. An orthodontic assembly according to claim 21 and including a latch for releasably retaining an archwire in the archwire passageway.

31. An orthodontic assembly according to claim 21 wherein the appliance is a buccal tube appliance.

32. An orthodontic assembly according to claim 21 wherein the appliance is an orthodontic bracket.

33. An orthodontic assembly according to claim 32 wherein the bracket is a self-ligating bracket.

34. An orthodontic appliance for a molar tooth comprising:
a base;
a body extending outwardly from the base, the body having an occlusal side, a gingival side, a mesial end and a distal end;
an elongated archwire passageway extending in a generally mesial-distal direction across the body for receiving an archwire, the archwire passageway having a generally flat lingual side, wherein the passageway includes a labial side that is closed; and
a groove extending along the occlusal side, the distal end and the gingival side of the body, wherein the groove is located directly adjacent the base and has a labial side, and wherein the labial side of the groove extends in a direction that is approximately parallel to the lingual side of the archwire passageway.

35. An orthodontic appliance according to claim 34 wherein the body includes a mesial end and a distal end, wherein the groove extends along the mesial end and the distal end, and wherein the groove is located in a lingual direction relative to the mesial end and the distal end.

36. An orthodontic appliance according to claim 34 wherein the groove has a height along a labial-lingual reference axis that is at least about 0.005 inch.

37. An orthodontic appliance according to claim 34 wherein the groove has a width along an occlusal-gingival reference axis that is at least about 0.005 inch.

38. An orthodontic appliance according to claim 34 wherein the groove has a certain length in a mesial-distal direction, and wherein the archwire passageway has a length in a mesial-distal direction that is larger than the mesial-distal length of the groove.

39. An orthodontic appliance according to claim 34 wherein the body includes a neck portion that is located directly adjacent the base and wherein the occlusal side and the gingival side extend past the neck portion in an occlusal-gingival direction.

* * * * *